United States Patent
Yoshizato et al.

(10) Patent No.: US 7,074,583 B2
(45) Date of Patent: Jul. 11, 2006

(54) METHOD FOR IDENTIFYING PHOSPHOPROTEIN

(75) Inventors: Katsutoshi Yoshizato, Higashihiroshima (JP); Dan Bach Kristensen, Odense C (DK)

(73) Assignees: Japan Science and Technology Corporation, Saitama (JP); Hiroshima Industrial Promotion Organization, Hiroshima (JP)

( * ) Notice: Subject to any disclaimer, the term of this patent is extended or adjusted under 35 U.S.C. 154(b) by 0 days.

(21) Appl. No.: 10/474,873

(22) PCT Filed: Apr. 4, 2002

(86) PCT No.: PCT/JP02/03384

§ 371 (c)(1),
(2), (4) Date: Feb. 10, 2004

(87) PCT Pub. No.: WO02/090969

PCT Pub. Date: Nov. 14, 2002

(65) Prior Publication Data

US 2004/0132125 A1 Jul. 8, 2004

(30) Foreign Application Priority Data

Apr. 10, 2001 (JP) ............................. 2001-111561

(51) Int. Cl.
*L12Q 1/42* (2006.01)
(52) U.S. Cl. ...................... 435/21; 435/68.1; 435/195; 356/344; 204/450
(58) Field of Classification Search ................. 435/21, 435/68.1, 195; 356/344; 204/450
See application file for complete search history.

(56) References Cited

OTHER PUBLICATIONS

Robert W. Leggett et al., The Journal of Biological Chemistry, Oct. 1995, vol. 270, No. 43, p. 25882.
M. Butler et al., Journal of Neurochemistry, 1986, vol. 47, No. 5, pp. 1520, 1521.

*Primary Examiner*—Leon B. Lankford, Jr.
(74) *Attorney, Agent, or Firm*—Wenderoth, Lind & Ponack, L.L.P.

(57) ABSTRACT

A method for identifying phosphoprotein, which comprises: subjecting a sample protein to two-dimensional electrophoresis; dephosphorylating the sample protein with phosphatase; once again performing the two-dimensional electrophoresis under the same conditions; and detecting the spot that migrates to the alkaline side of the isoelectric focusing as the phosphoprotein is provided as a convenient method for identifying phosphoprotein with high accuracy.

2 Claims, 1 Drawing Sheet

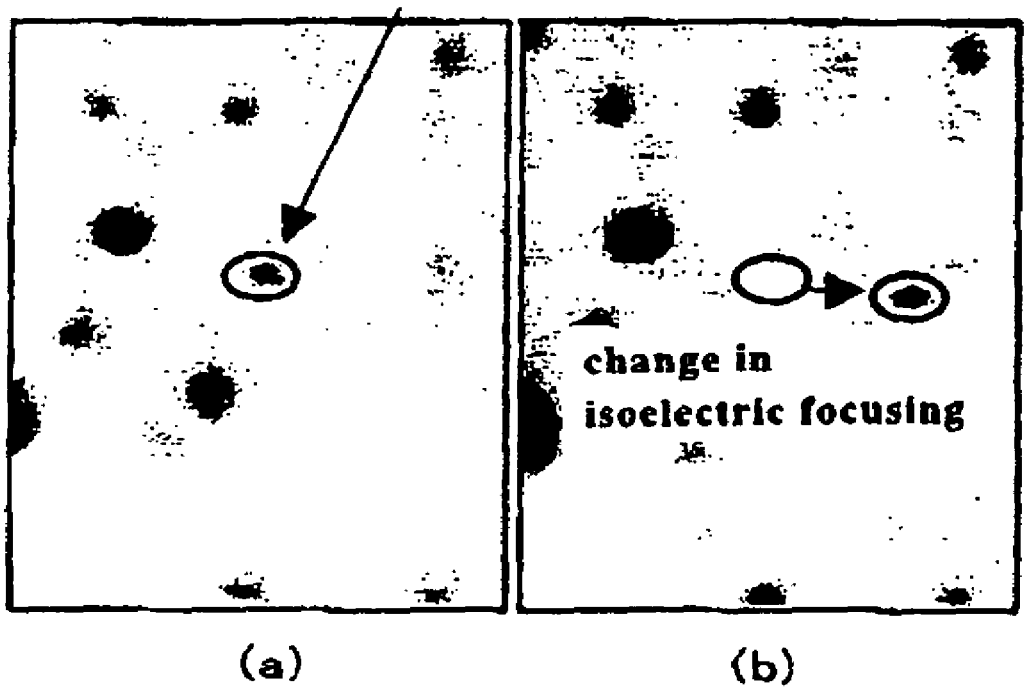

METHOD FOR IDENTIFYING PHOSPHOPROTEIN

TECHNICAL FIELD

The invention of the present application relates to a method for identifying phosphoprotein. More specifically, the invention of the present application relates to a method for distinctively detecting, isolating and identifying phosphoprotein from a sample protein.

BACKGROUND ART

Proteins, after being transcribed and translated from genome, are subjected to posttranslational modifications such as phosphorylation, which directly influence functions such as signal pathway and enzymatic activity. Since proteins change qualitatively or quantitatively with development of life, differentiation, progression of diseases, environmental changes and the like, by analyzing a set of proteins (proteome) encoded by a genome, proteins may be understood cyclopaedically, and significant knowledge on the analysis of bioinformatics, the diagnosis of diseases and the development of drugs may be obtained. Especially, phosphorylation of proteins, one type of posttranslational modification of genes, is an important step in signal transmission, activation of enzymes or the like. Consequently, identification of phosphoproteins is important to understand functions of proteins.

Up to now, gel electrophoresis has been generally used as a method for identifying proteins. Specifically, a two-dimensional gel electrophoresis method has found wide acceptance because it enables the separation of proteins in high separability. Further, to distinguish phosphoprotein from the various proteins developed on the two-dimensional gel electrophoresis, immunostaining method that uses antibody and labeling method that uses radioisotopes have been known. Specifically, a protein separated by electrophoresis is immobilized on a hydrophobic membrane, and brought into contact with an antibody, for which its antigen is the desired phosphoprotein, to form an antigen-antibody complex, which is then detected with a secondary antibody labeled with an enzyme or a radioisotope.

However, these conventional methods were problematic in that they are intricate and time-consuming, and for the methods that uses radioisotopes, special facilities are required and are dangerous.

Under these circumstances, the invention of the present application has been made, and aims to provide, upon solving the problems of the prior art, a convenient method for identifying phosphoprotein in less time.

DISCLOSURE OF INVENTION

For solving the foregoing problems, the invention of the present application firstly provides a method for identifying phosphoprotein, which comprises: subjecting a sample protein to two-dimensional electrophoresis; dephosphorylating the sample protein with phosphatase; once again performing the two-dimensional electrophoresis under the same conditions; and detecting the spot that migrates to the alkaline side of the isoelectric focusing as the phosphoprotein.

The invention of the present application secondly provides, as an embodiment, the method for identifying phosphoprotein, wherein the sample protein is dephosphorylated after solubilizing the sample protein, and adding a preservation buffer to prevent precipitation of the protein and deactivation of the phosphatase.

And, the invention of the present application thirdly provides the method for identifying phosphoprotein, wherein the preservation buffer contains a surfactant along with a transition metal salt.

BRIEF DESCRIPTION OF DRAWING

FIG. 1 shows the two-dimensional electrophoresis gel image obtained in the Example of the present application. (a: before PPase treatment, b: after PPase treatment, arrow: migrating protein)

BEST MODE FOR CARRYING OUT THE INVENTION

The method for identifying phosphoprotein of the present invention is based on the principle that: after subjecting a sample protein containing phosphoprotein to a two-dimensional electrophoresis, dephosphorylating the protein using phosphatase, and once again subjecting it to a two-dimensional electrophoresis, only the spot corresponding to the dephosphorylated protein migrates towards the alkaline side on the isoelectric focusing. Thus, phosphoprotein can be detected conveniently and identified by simply comparing the results of the two-dimensional electrophoreses before and after treating the sample protein with phosphatase.

However, new problems have arisen for this identification method. That is, since the concentration of a sample protein used in ordinary proteome analysis is extremely high, precipitation of the protein tends to occur, and phosphatase can not work.

The present inventors have assiduously conducted investigations, and have found that by solubilizing protein using a surfactant such as SDS (Sodium dodecyl sulfate) and adding a preservation buffer, precipitation of the protein can be prevented and dephosphorylation can be conducted without deactivating the phosphatase. First, the inventors have focused on SDS as a component that prevents precipitation of the protein. However, since the use of high concentrations of a surfactant such as SDS deactivates phosphatase, transition metal salts were found to be effective for stabilizing phosphatase.

Thus, as the preservation buffer capable of preventing both the precipitation of protein and the deactivation of phosphatase, which contains a surfactant and a transition metal salt, various buffers have been studied. According to the studies by the present inventors, alkyl sulfates such as SDS as well as alkyl sulfonates are preferable as the surfactant, and halides, sulfates and the like of polyvalent transition metals, especially metals of group III to group VIII in the periodic table, such as Mn, Sn, V, W, Mo, Ta, Ga, Sb, Fe, Ni and rare earth elements, are preferable as the transition metal salt.

Of course, in addition to the surfactant and the transition metal salt, various compounds known as a buffer component, such as EDTA salt, polyether compound, polyether ester compound and thioether compound, may be incorporated. In the present invention, the addition of SDS, Tris-HCl (pH 7.5), $Na_2EDTA$, DTT, Brij35 and $MnCl_2$ are especially favorable, since the preservation buffer becomes highly effective in preventing precipitation of protein and stabilizing phosphatase. A specific example of the composition of the preservation buffer may be, for example, in the following range.

SDS: 0.1 to 0.3%
Tris-HCl (pH 7.5): 1.5 to 3.5 mM
$Na_2EDTA$: 2 to 10 μM
DTT: 100 to 300 μM
Brij35: 0.0001 to 0.001%
$MnCl_2$: 0.05 to 0.2 mM With respect to the foregoing composition of the preservation buffer, its usefulness has been clarified by assiduous investigations of the present inventors. The addition of this preservation buffer enables to prevent precipitation of the protein and allows phosphatase to effectively work; thus by comparing the results of the two-dimensional electrophoreses before and after the treatment, the dephosphorylated protein can be detected conveniently with certainty. Further, by cutting out the spot whose position in the two-dimensional electrophoresis has changed from the gel and washing by general methods, phosphoprotein can be isolated. Furthermore, the specific structure or the like of such phosphoproteins can also be determined and identified by comparing the results of the two-dimensional electrophoreses to various two-dimensional electrophoresis gel proteome databases.

Hereinafter, the embodiment of this invention is illustrated more specifically by referring to the following Examples. Of course, this invention is not limited to the following Examples, and it goes without saying that various modifications are possible in the details.

EXAMPLE

Example 1

Protein (100 μg/50 μg) derived from rat skin fibroblasts adjusted for two-dimensional electrophoresis and 10% SDS (20 μl) were added to a 1.5 mL-Eppendorf tube, vigorously stirred, and allowed to stand in an sonicator for 1 minute. Purified water (920 μl) was added, and the mixture was stirred, followed by the addition of a preservation buffer and stirring of the mixture. The composition of the preservation buffer was as follows.

Tris-HCl (pH 7.5): 50 mM
$Na_2$EDTA: 0.1 mM
DTT: 5 mM
Brij35 (0.01%): >5 μl
$MnCl_2$ (20 mM): 5 μl The resulting protein solution was divided into two parts, and recombinant λ protein phosphatase (PPase) (manufactured by New England Biolabs, 1 μl: 400 U) was added to one part, and the mixture was warmed at 30° C. for 1 hour. This solution was concentrated to 20 μl using a Millipore Ultra Free centrifugal filter; a buffer for two-dimensional electrophoresis (5 M Urea, 2 M thiourea, 1% DTT, 2% CHAPS, 2% SB3-10, 1% Ampldine) was then added to adjust the total volume to 500 μl, and two-dimensional electrophoreses was performed.

The primary electrophoresis was performed using a Pharmacia Hoefer Multiple II electrophoresis chamber. The secondary SDS-PAGE was performed on a 9 to 18% acrylamide gradient gel using an Iso-Dalt system (manufactured by Pharmacila Hoefer).

The proteins were visualized by silver staining, and the two-dimensional electrophoresis gel was imaged with an Epson ES800 scanner.

Image analysis and search of the two-dimensional electrophoresis gel proteome database were performed using Melanie II 2-D Page Software Package (manufactured by Bio-Rad, version 2.2).

The resulting images of the two-dimensional electrophoresis gel are shown in FIG. 1. Migration of the spot with the arrow was observed after the PPase treatment (b).

This spot was cut out from the gel, and search of the database was conducted, which led to the results as shown in the following Table 1.

TABLE 1

Phosphoproteins of rat skin fibroblasts
14-3-3 protein epsilon
60s acidic ribosomal protein p0
Cofilin, non-muscle isoform
Calponin 3
Destrin
Elongation factor 1-beta
Elongation factor 1-delta
Heterogeneous nuclear ribonucleoprotein
Myosin light chain alkali
Myosin regulatory light chain
Nucleolar phosphoprotein B23
Osteoclast stimulating factor
Proteosome component C8*
Small glutamine-rich tetratricopeptide repeat-containing protein*
SRC substrate cortactin From the table, phosphoproteins of rat skin fibroblasts, including two types of proteins (*) for which phosphorylation have not been reported so far, were detected as candidate proteins.

INDUSTRIAL APPLICABILITY

As has been described in detail above, the present invention provides a convenient method by which phosphoprotein can be identified in high accuracy. Since phosphorylation of protein is a significant step in signal transmission, activation of enzymes or the like, various information on the functions of protein may be obtained by identifying phosphoprotein. Since the method of the present invention enables accurate identification of phosphoprotein in only a short period of time, development of novel methods for diagnosing diseases and new drugs may be expected.

The invention claimed is:

1. A method for identifying phosphoprotein from sample proteins, which comprises the steps of:
   (i) solubilizing the sample proteins;
   (ii) adding a preservations buffer to the sample proteins solution to prevent precipitation of the proteins and deactivation of phosphatase;
   (iii) dividing the sample proteins solution into two parts, sample "a" and sample "b";
   (iv) dephosphorylating the sample "b" with phosphatase;
   (v) subjecting the sample "a" and the sample "b" to two-dimensional electrophoresis under same conditions, thereby spotting each sample protein on electrophoresis gel "a" and electrophoresis gel "b", respectively;
   (vi) comparing protein spots on the electrophoresis gel "b" with those on the electrophoresis gel "a"; and
   (vii) identifying the protein of which spot position on the electrophoresis gel "b" is migrated to the alkaline side of the isoelectric focusing compared with the corresponding spot on the electrophoresis gel "a" as the phosphoprotein.

2. The method for identifying phosphoprotein as claimed in claim 1, wherein the preservation buffer contains a surfactant along with a transition metal salt.

* * * * *